US009073086B2

(12) United States Patent
Jung et al.

(10) Patent No.: US 9,073,086 B2
(45) Date of Patent: Jul. 7, 2015

(54) PROBE FOR ULTRASONIC DIAGNOSTIC APPARATUS AND METHOD OF MANUFACTURING THE SAME

(75) Inventors: Jin Woo Jung, Seoul (KR); Jeong Cheol Seo, Gwangju-si (KR); Jae Yk Kim, Seoul (KR)

(73) Assignee: SAMSUNG MEDISON CO., LTD., Hongcheon-Gun, Gangwon-Do (KR)

( * ) Notice: Subject to any disclaimer, the term of this patent is extended or adjusted under 35 U.S.C. 154(b) by 220 days.

(21) Appl. No.: 12/725,362

(22) Filed: Mar. 16, 2010

(65) Prior Publication Data

US 2010/0241003 A1 Sep. 23, 2010

(30) Foreign Application Priority Data

Mar. 18, 2009 (KR) ........................ 10-2009-0023013

(51) Int. Cl.
*A61B 5/05* (2006.01)
*B06B 1/06* (2006.01)
*G10K 11/00* (2006.01)

(52) U.S. Cl.
CPC ......... *B06B 1/0622* (2013.01); *Y10T 29/49005* (2015.01); *G10K 11/004* (2013.01)

(58) Field of Classification Search
USPC .......................................... 600/407, 437–475
See application file for complete search history.

(56) References Cited

U.S. PATENT DOCUMENTS 5,637,800 A * 6/1997 Finsterwald et al. ........... 73/642
6,104,126 A 8/2000 Gilmore
6,308,389 B1 * 10/2001 Tezuka ......................... 29/25.35
2003/0085635 A1 5/2003 Davidsen
2005/0225210 A1 10/2005 Englund et al.
2007/0157732 A1 7/2007 Lee et al.

FOREIGN PATENT DOCUMENTS

EP 2 025 414 A1 2/2009
JP 63-212299 A 9/1998
JP 2006-095178 A 4/2006
JP 2007-158467 A 6/2007
JP 2009-038675 A 2/2009

OTHER PUBLICATIONS

Extended European Search Report issued in European Patent Application No. EP 1015255.8 dated Jul. 20, 2010.
Japanese Office Action issued in Japanese Application No. 2010-058053 dated Jul. 22, 2014.

* cited by examiner

*Primary Examiner* — Mark Remaly
(74) *Attorney, Agent, or Firm* — McDermott Will & Emery LLP

(57) ABSTRACT

A probe for an ultrasonic diagnostic apparatus includes a backing layer including backing members, a first connector bonded between the backing members and including electrodes spaced from each other in an arrangement direction, and a piezoelectric member electrically connected to the electrodes. A method of manufacturing the same is also disclosed. The piezoelectric member is connected to the first connector or to first and second connectors via an electrode layer instead of using a complicated and laborious soldering operation, thereby enabling easy connection between the piezoelectric member and the connector while preventing deterioration in performance caused by defective connection therebetween and deterioration in performance of the piezoelectric member caused by heat during manufacturing operation.

9 Claims, 12 Drawing Sheets

PROBE FOR ULTRASONIC DIAGNOSTIC APPARATUS AND METHOD OF MANUFACTURING THE SAME

CROSS-REFERENCE TO RELATED APPLICATIONS

The present application claims priority from Korean Patent Application No. 10-2009-0023013 filed on Mar. 18, 2009, the entire subject matter of which is incorporated herein by reference.

BACKGROUND OF THE INVENTION

1. Field of the Invention

The present invention relates to probes and, more particularly, to a probe for an ultrasonic diagnostic apparatus that generates internal images of a patient body using ultrasound waves, and a method of manufacturing the same.

2. Description of the Related Art

Generally, an ultrasonic diagnostic apparatus refers to a non-invasive apparatus that irradiates an ultrasound signal from a surface of a patient body towards a target internal organ beneath the body surface and obtains an image of a monolayer or blood flow in soft tissue from information in the reflected ultrasound signal (ultrasound echo-signal). The ultrasonic diagnostic apparatus has been widely used for diagnosis of the heart, the abdomen, the urinary organs, and in obstetrics and gynecology due to various merits such as small size, low price, real-time image display, and high stability through elimination of radiation exposure, as compared with other image diagnostic systems, such as X-ray diagnostic systems, computerized tomography scanners (CT scanners), magnetic resonance imagers (MRIs), nuclear medicine diagnostic apparatuses, and the like.

The ultrasonic diagnostic apparatus includes a probe which transmits an ultrasound signal to a patient body and receives the ultrasound echo-signal reflected therefrom to obtain the ultrasound image of the patient body.

The probe includes a transducer, a case with an open upper end, a cover coupled to the open upper end of the case to directly contact the body surface of the patient, and the like.

The transducer includes a piezoelectric layer in which a piezoelectric material converts electrical signals into sound signals or vice versa while vibrating, a sound matching layer reducing a difference in sound impedance between the piezoelectric layer and a patient body to allow as much of the ultrasound waves generated from the piezoelectric layer as possible to be transferred to the patient body, a lens layer focusing the ultrasound waves, which travel in front of the piezoelectric layer, onto a predetermined point, and a backing layer blocking the ultrasound waves from traveling in a rearward direction of the piezoelectric layer to prevent image distortion.

The piezoelectric layer includes a piezoelectric member and electrodes provided to upper and lower ends of the piezoelectric member, respectively. Further, a printed circuit board (PCB) is bonded to the piezoelectric layer. The PCB is provided with wiring electrodes that are connected to the electrodes of the piezoelectric layer to transfer signals from the piezoelectric member. The PCB is connected to the piezoelectric layer by connecting the wiring electrodes of the PCB and the electrodes of the piezoelectric layer.

In fabrication of the probe, connection of the wiring electrodes of the PCB to the electrodes of the piezoelectric layer is a laborious operation, which increases fabrication time and causes deterioration in performance of the probe due to low durability and non-uniformity of a connected part therebetween. Therefore, there is a need to provide a probe for an ultrasonic diagnostic apparatus that overcomes such problems.

SUMMARY OF THE INVENTION

The present invention is conceived to solve the problems of the related art as described above, and an aspect of the present invention is to provide an improved probe for an ultrasonic diagnostic apparatus configured to allow easy manufacture of the probe while preventing deterioration in performance caused by defective connection between a piezoelectric layer and a PCB, and a method of manufacturing the same.

In accordance with one aspect of the invention, a probe for an ultrasonic diagnostic apparatus includes: a backing layer including backing members; a first connector bonded between the backing members and including electrodes spaced from each other in an arrangement direction; and a piezoelectric member electrically connected to the electrodes.

The first connector may be disposed in a height direction of the backing members.

The first connector may include a flexible printed circuit board (FPCB).

The backing layer may include an electrode layer electrically connected to the electrodes.

The electrode layer may be formed on a surface of the backing layer.

The backing layer may be formed with a mounting groove, and the piezoelectric member may be inserted into the mounting groove.

The probe may further include a second connector bonded between the backing members and including electrodes spaced from each other in the arrangement direction.

The second connector may be disposed in the height direction of the backing members such that the electrodes of the first connector alternate with the electrodes of the second connector.

The electrodes of the first and second connectors may be signal electrodes.

In accordance with another aspect of the invention, a method of manufacturing a probe for an ultrasonic diagnostic apparatus includes: forming electrodes on a first connector to be spaced from each other in an arrangement direction; forming a backing layer by bonding the first connector between backing members; and stacking a piezoelectric member on the backing layer to be electrically connected to the electrodes.

The method may further include forming an electrode layer on the backing layer to be electrically connected to the piezoelectric member and the electrodes after forming the backing layer.

The forming a backing layer may include disposing the first connector in a height direction of the backing members.

In accordance with a further aspect of the invention, a method of manufacturing a probe for an ultrasonic diagnostic apparatus includes: forming electrodes on a first connector to be spaced from each other in an arrangement direction; forming electrodes on a second connector to be spaced from each other in the arrangement direction; forming a backing layer by bonding the first and second connectors between backing members; and stacking a piezoelectric member on the backing layer to be electrically connected to the electrodes of the first and second connectors.

The method may further include forming an electrode layer on the backing layer to be electrically connected to the piezoelectric member and the electrodes of the first and second connectors after forming the backing layer.

The forming a backing layer may include disposing the second connector in a height direction of the backing members such that the electrodes of the first connector alternate with the electrodes of the second connector.

The method may further include forming a mounting groove on the backing layer, wherein the stacking a piezoelectric member on the backing layer includes inserting the piezoelectric member into the mounting groove.

BRIEF DESCRIPTION OF THE DRAWINGS

The above and other aspects, features and advantages of the invention will become apparent from the following description of embodiments given in conjunction with the accompanying drawings, in which.

DETAILED DESCRIPTION OF THE EMBODIMENT

Exemplary embodiments of the invention will now be described in detail with reference to the accompanying drawings. It should be noted that the drawings are not to precise scale and may be exaggerated in thickness of lines or size of components for descriptive convenience and clarity only. Furthermore, terms used herein are defined by taking functions of the invention into account and can be changed according to the custom or intention of users or operators. Therefore, definition of the terms should be made according to overall disclosures set forth herein.

Figure 1:
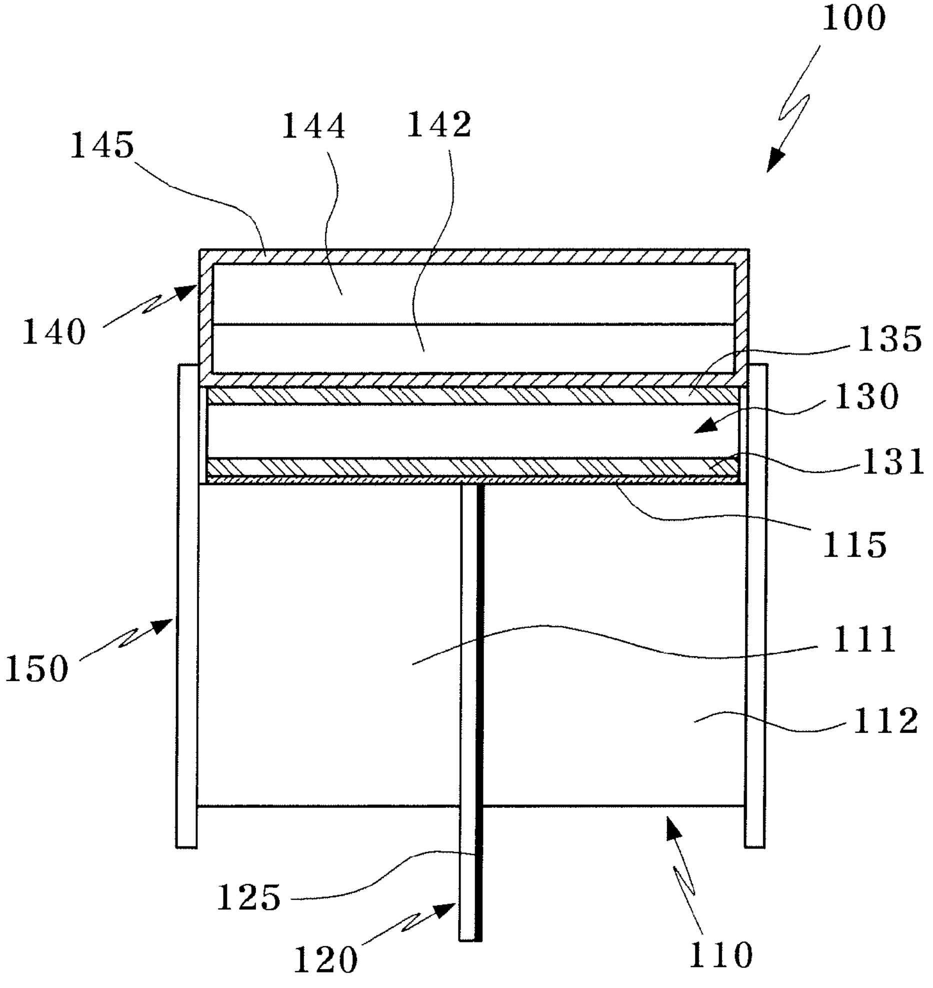
FIGS. 1 and 2 are schematic views of a probe for an ultrasonic diagnostic apparatus according to a first embodiment of the present invention.
Figure 2:
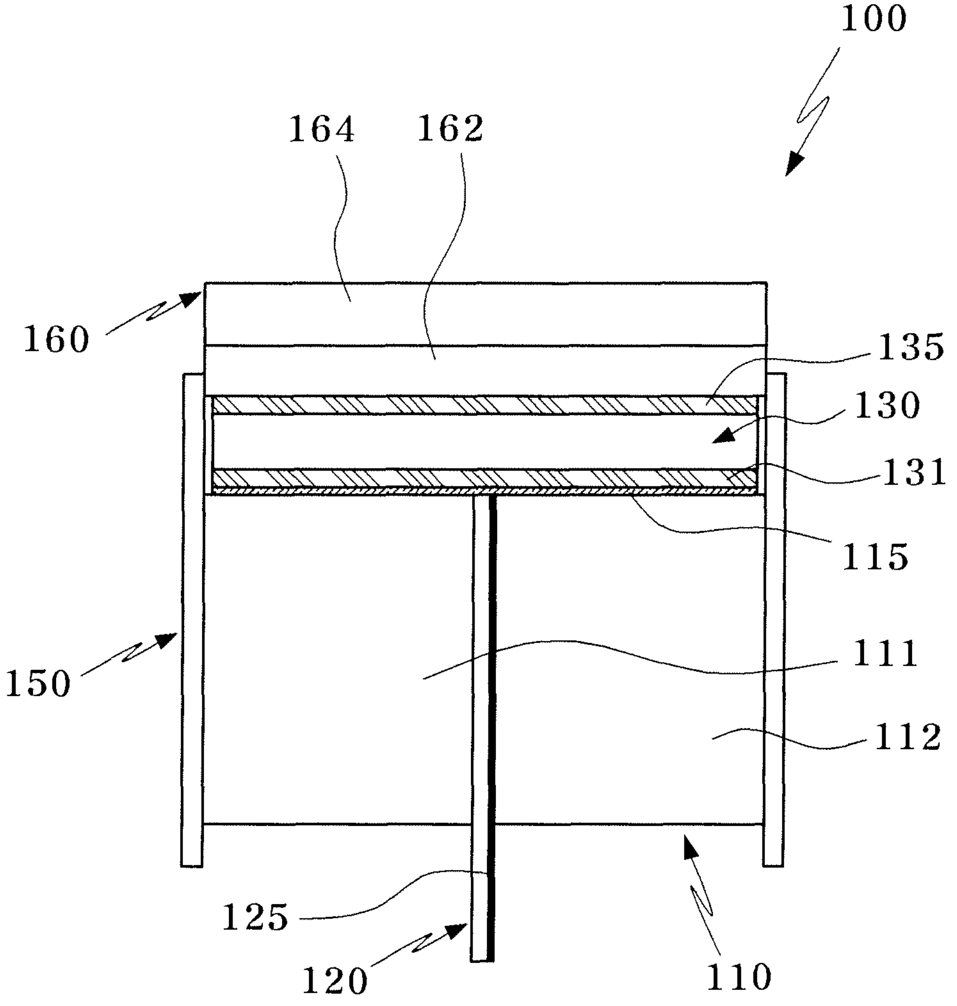

FIGS. 1 and 2 are schematic views of a probe for an ultrasonic diagnostic apparatus according to a first embodiment of the present invention.

Referring to FIG. 1, a probe 100 for an ultrasonic diagnostic apparatus according to this embodiment includes a backing layer 110, a first connector 120, and a piezoelectric member 130.

The backing layer 110 is disposed behind the piezoelectric member 130 described below. The backing layer 110 reduces a pulse width of an ultrasound wave by suppressing free vibration of the piezoelectric member 130 and prevents image distortion by blocking unnecessary propagation of the ultrasound wave in the rearward direction of the piezoelectric member 130.

The backing layer 110 includes multiple backing members 111, 112 and is formed by bonding the backing members 111, 112 to each other. The backing layer 110 may be formed of a material containing a rubber to which epoxy, tungsten powder, and the like are added.

The first connector 120 includes an insulation part (reference numeral omitted) and electrodes 125. The multiple electrodes 125 are disposed on the insulation part to be separated from each other in an "arrangement direction." Herein, the term "arrangement direction" refers to a direction in which piezoelectric members are arranged in an array. In other words, the electrodes 125 are spaced from each other in the arrangement direction of piezoelectric members 130 which are arranged in an array (see FIG. 4).

In this embodiment, each of the electrodes 125 of the first connector 120 is a signal electrode that is electrically connected to a first electrode 131 of the piezoelectric member 130 described below.

The first connector 120 including the electrodes 125 is bonded between the backing members 111, 112. According to this embodiment, the first connector 120 is inserted and bonded between two backing members 111, 112.

The first connector 120 is disposed in a "height direction of the backing members 111, 112." The backing members 111, 112 are bonded to opposite sides of the first connector 120, thereby forming the backing layer 110. Herein, the term "height direction of the backing members 111, 112" refers to a direction perpendicular to a direction in which an electrode layer 115 is formed (see FIG. 4).

One end of the first connector 120 bonded between the backing members 111, 112 is exposed on a front side of the backing layer 110 adjacent to the piezoelectric member 130, and the other end thereof extends through a rear side of the backing layer 110. As such, since the one end of the first connector 120 is exposed on the front side of the backing layer 110, the electrodes 125 of the first connector 120 are exposed on the front side of the backing layer 110.

The first connector 120 may include a flexible printed circuit board (FPCB), a printed circuit board (PCB) or any configuration capable of supplying signals or electricity.

The backing layer 110 includes the electrode layer 115. The electrode layer 115 is formed on the backing layer 110 to be disposed between the backing layer 110 and the piezoelectric member 130. The electrode layer 115 is electrically connected to the electrodes 125.

According to this embodiment, the electrode layer 115 is formed on a surface of the backing layer 110. Specifically, the electrode layer 115 may be formed on the front surface of the backing layer 110 adjacent to the piezoelectric member 130. The electrode layer 115 may be formed of a highly electrically conductive material by deposition, sputtering, plating, spraying or the like.

The piezoelectric member 130 is electrically connected to the electrodes 125. The piezoelectric member 130 generates ultrasound waves using a resonance phenomenon and may be formed of a ceramic of lead zirconate titanate (PZT), a PZNT single crystal made of a solid solution of lead zinc niobate and lead titanate, a PZMT single crystal made of a solid solution of lead magnesium niobate and lead titanate, or the like.

The piezoelectric member 130 is formed with first and second electrodes 131, 135. One of the first and second electrodes 131, 135 is disposed on one side of the piezoelectric member 130 and the other electrode is disposed on the other side thereof. Here, the first electrode 131 is electrically connected to the electrode layer 115.

The first and second electrodes 131, 135 may be formed of a highly electrically conductive metal. Here, one of the first and second electrodes 131, 135 serves as a positive pole or signal electrode of the piezoelectric member 130, and the other serves as a negative pole or ground electrode of the piezoelectric member 130.

The first and second electrodes 131, 135 are separated from each other to allow the signal electrode and the ground electrode to be separated from each other. In this embodiment, the first and second electrodes 131, 135 are illustrated as serving as the positive and negative poles, respectively.

According to this embodiment, the piezoelectric member 130 is electrically connected to the electrodes 125 via the electrode layer 115 and the first electrode 131 which are electrically connected to each other.

The piezoelectric member 130 may be composed of a plurality of piezoelectric members 130 arranged in an array to provide multiple channels. The electrode layer 115 may also be composed of a plurality of electrode layers 115 arranged side by side in an array so as to correspond to the piezoelectric members 130 arranged in an array. Therefore, the piezoelectric members 130 and the electrode layers 115 are correspondingly connected to the electrodes 125 spaced from each other in the arrangement direction.

According to this embodiment, the probe 100 may further include a sound matching layer 140 and a ground connector 150.

The sound matching layer 140 is disposed in front of the piezoelectric member 130. The sound matching layer 140 allows ultrasound signals generated from the piezoelectric member 130 to be efficiently transferred to a target by matching sound impedances of the piezoelectric member 130 and the target. The sound matching layer 140 is configured to have an intermediate value between the sound impedance of the piezoelectric member 130 and the sound impedance of the target.

The sound matching layer 140 may be formed of a glass or resin material, and includes a first sound matching layer 142 and a second sound matching layer 144, which are formed of different materials to allow the sound impedance of the sound matching layer 140 to be changed stepwise from the piezoelectric member 130 to the target.

The sound matching layer 140 further includes an electrode part 145. The electrode part 145 may be formed to partially or entirely surround the sound matching layer 140. When the electrode part 145 is formed to partially surround the sound matching layer 140, the electrode part 145 surrounds the first sound matching layer 142 adjacent to the piezoelectric member 130.

Like the electrode layer 115, the electrode part 145 may be formed of a highly electrically conductive material by deposition, sputtering, plating, spraying or the like.

The electrode part 145 is electrically connected to a second electrode 135 of the piezoelectric member 130. As a result, the piezoelectric member 130 is electrically connected to the electrode part 145.

The ground connector 150 is electrically connected to the electrode part 145. As in the first connector 120, the ground connector 150 may include a flexible printed circuit board (FPCB), a printed circuit board, or any configuration capable of supplying signals or electricity. The ground connector 150 may be connected to the electrode part 145 by a soldering material such as lead, an anisotropic conductor, and the like. As such, the ground connector 150 is electrically connected to the second electrode 135 of the piezoelectric member 130 via connection with the electrode part 145.

According to this embodiment, connection between the piezoelectric member 130 and the ground connector 150 is illustrated as being obtained through the electrode part 145 formed on the sound matching layer 140. However, the invention is not limited to this configuration, and the connection between the piezoelectric member 130 and the ground connector 150 may be embodied in various ways.

For example, referring to FIG. 2, a sound matching layer 160 including the first and second sound matching layers 162, 164 is directly connected to the piezoelectric member 130. In other words, the sound matching layer 160 is formed of an electrically conductive material, such as graphite, gold, silver or copper, and is electrically connected to the second electrode 135 of the piezoelectric member 130.

The sound matching layer 160 may be entirely or partially formed of the electrically conductive material. When the sound matching layer 160 is partially formed of the electrically conductive material, the first sound matching layer 162 adjacent to the piezoelectric member 130 may be formed of the electrically conductive material.

Although not shown in the drawings, the probe 100 according to this embodiment may further include a lens layer disposed in front of the sound matching layer 140 to focus forwardly traveling ultrasound waves on a predetermined point.

The probe 100 for an ultrasonic diagnostic apparatus according to this embodiment may be a linear type probe having a linear surface or a convex type probe having a convexly rounded surface or a phased array probe.

Figure 3:
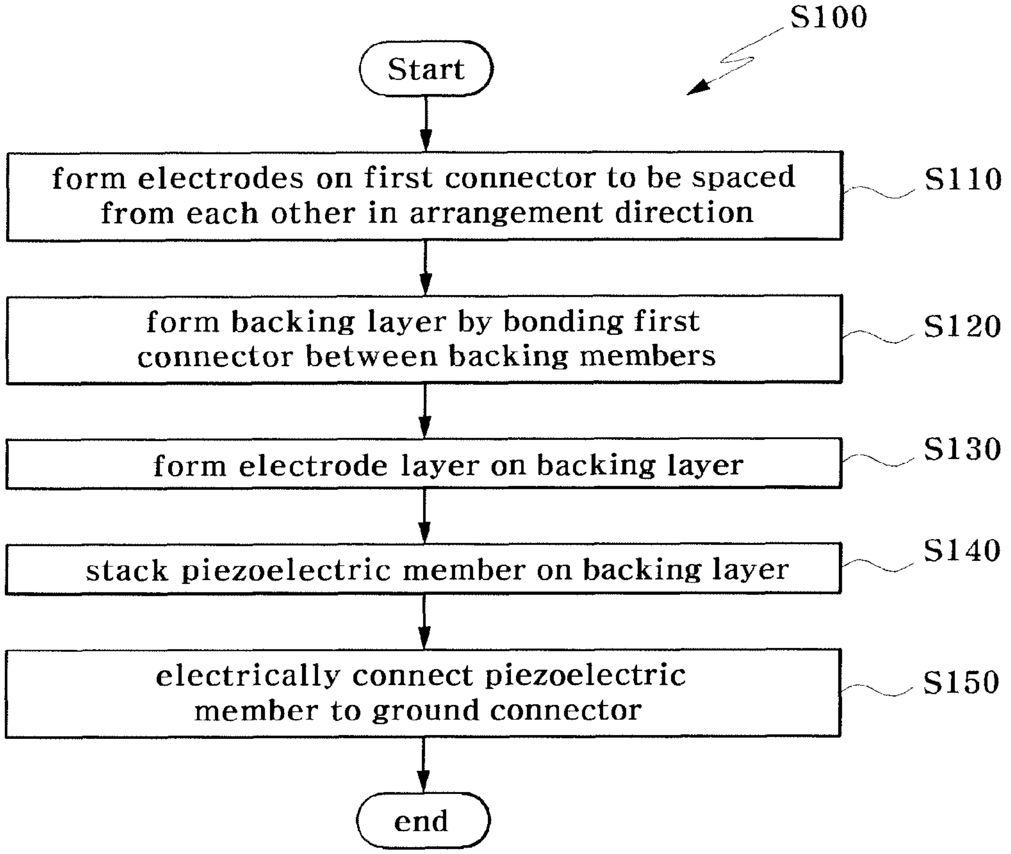
FIG. 3 is a flowchart of a method of manufacturing the probe for an ultrasonic diagnostic apparatus according to the first embodiment of the invention.
Figure 4:
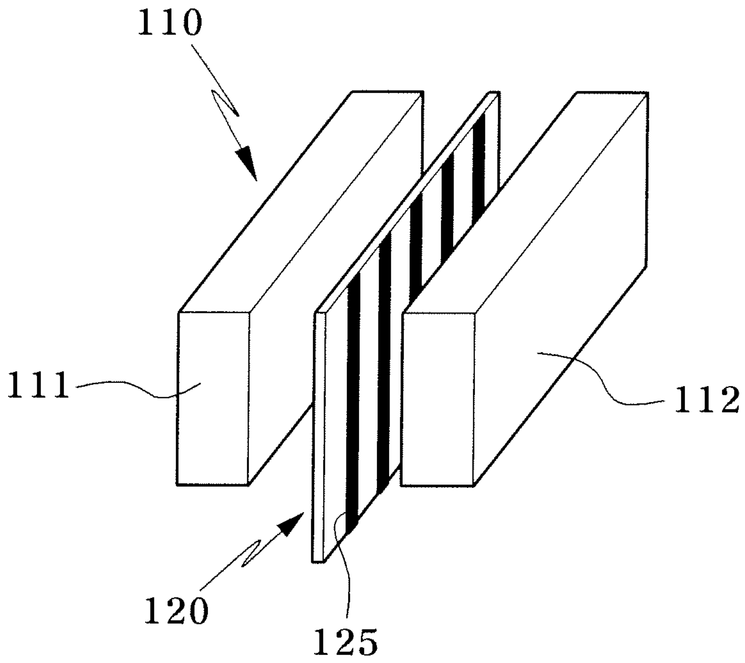
FIGS. 4 and 5 are views of a process of forming a backing layer of the probe according to the first embodiment of the invention.
Figure 5:
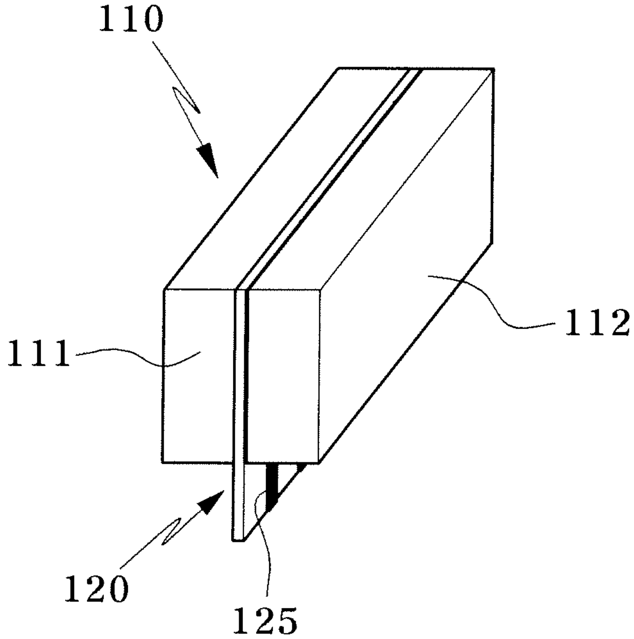
Figure 6:
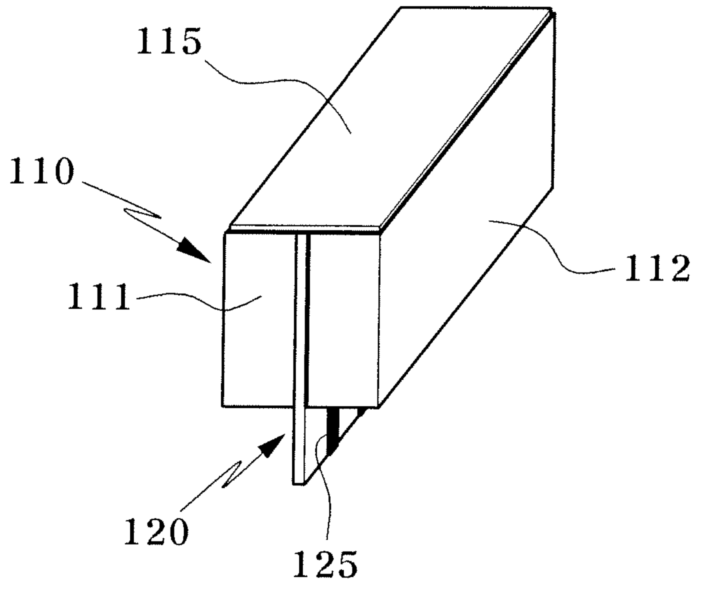
FIG. 6 is a view of a process of forming an electrode layer on the backing layer of the probe according to the first embodiment of the invention.

FIG. 3 is a flowchart of a method of manufacturing the probe for an ultrasonic diagnostic apparatus according to the first embodiment of the invention, FIGS. 4 and 5 are views of a process of forming the backing layer of the probe according to the first embodiment of the invention, and FIG. 6 is a view of a process of forming the electrode layer on the backing layer of the probe according to the first embodiment of the invention.

Referring to FIGS. 1 to 6, the method of manufacturing the probe for an ultrasonic diagnostic apparatus according to the first embodiment will now be described.

In the method S100 according to this embodiment, firstly, electrodes 125 are formed on a first connector 120, as shown in FIG. 4, in S110.

The respective electrodes 125 are formed in the height direction of backing members 111, 112 and are spaced from each other in the arrangement direction in which piezoelectric members 130 are arranged.

In this embodiment, the first connector 120 includes, but is not limited to, a flexible printed circuit board (FPCB). The first connector 120 may include a printed circuit board or any configuration capable of supplying signals or electricity as well as the flexible printed circuit board (FPCB).

With the electrodes 125 formed on the first connector 120, the first connector 120 is bonded between backing members 111, 112 to form a backing layer 110, as shown in FIG. 5, in S120.

For this purpose, the backing members 111, 112 are formed of a material including a rubber to which epoxy resin, tungsten powder, and the like are added. Then, with the first connector 120 disposed between the backing members 111, 112 in the height direction, the backing members 111, 112 are bonded to opposite sides of the first connector 120, thereby completing formation of the backing layer 110.

One end of the first connector 120 bonded between the backing members 111, 112 is exposed on the front side of the backing layer 110 adjacent to the piezoelectric member 130, and the other end thereof extends through the rear side of the backing layer 110.

Since the one end of the first connector 120 is exposed on the front side of the backing layer 110, the electrodes 125 of the first connector 120 are exposed one the front side of the backing layer 110.

After the backing layer 110 is formed, an electrode layer 115 is formed on the backing layer 110 to be electrically connected to the piezoelectric member 130 and the electrodes 125 in S130.

According to this embodiment, the electrode layer 115 is formed on a surface of the backing layer 110. Specifically, the electrode layer 115 may be formed on the front surface of the backing layer 110 adjacent to the piezoelectric member 130. The electrode layer 115 may be formed of a highly electrically conductive material by deposition, sputtering, plating, spraying or the like.

With this configuration of the electrode layer 115, the rear side of the electrode layer 115 adjoining the surface of the backing layer 110 is electrically connected to the electrodes 125 of the first connector 120.

After the electrode layer 115 is formed on the backing layer 110, the piezoelectric member 130 is stacked on the backing layer 110 to be electrically connected to the electrodes 125 in S140.

By this process, a first electrode 131 of the piezoelectric member 130 is electrically connected to the electrode layer 115. As such, since the electrode layer 115 connected to the first electrode 131 is electrically connected to the electrodes 125 of the first connector 120, the piezoelectric member 130 is electrically connected to the electrodes 125 via the electrode layer 115 and the first electrode 131 which are electrically connected to each other.

According to this embodiment, the piezoelectric member 130 may be divided into multiple piezoelectric members 130 spaced a predetermined distance from each other and arranged side by side in an array, so that the multiple piezoelectric members 130 can be used as multiple channels corresponding to the multiple electrodes 125 formed on the first connector 120, respectively.

The electrode layer 115 may also be divided into multiple electrode layers, which are arranged side by side in an array so as to correspond one-to-one to first electrodes 131 formed on the multiple piezoelectric members 130.

According to this embodiment, stacks of the backing layer 110 and the piezoelectric member 130 are diced by a dicing machine (not shown). Dicing is performed to a depth such that the electrode layer 115 can be reliably divided into the multiple electrode layers.

By dicing, the piezoelectric member 130 is divided into the multiple piezoelectric members 130 spaced a predetermined distance from each other, such that first and second electrodes 131, 135 formed on each of the piezoelectric members 130 can be electrically completely separated from first and second electrodes 131, 135 formed on other piezoelectric members 130 adjacent thereto.

When the electrode layer 115 is divided into the multiple electrode layers 115 by dicing, each of the electrodes layers 115 is electrically completely separated from other electrode layers 115 adjacent thereto such that only one divided electrode layer 115 is connected to a first electrode 131 of one piezoelectric member 130.

In this embodiment, the electrode layer 115 is illustrated as being diced together with the piezoelectric member 130 to correspond to the first electrode 131 of the piezoelectric member 130. However, the invention is not limited thereto. Alternatively, the electrode layer 115 may be subjected to a patterning process to correspond to the first electrode 131 by optical etching, etching or the like before the piezoelectric member 130 is stacked on the backing layer 110.

After the piezoelectric member 130 is stacked on the backing layer 110, the piezoelectric member 130 is electrically connected to a ground connector 150, as shown in FIG. 1, in S150.

The ground connector 150 may be electrically connected to the piezoelectric member 130 via electrical connection between the second electrode 135 and an electrode part 145 formed on a sound matching layer 140. Alternatively, the ground connector 150 may be electrically connected to the piezoelectric member 130 via electrical connection between the second electrode 135 and a sound matching layer 140, which is made of an electrically conductive material, as shown in FIG. 2.

The method S100 of manufacturing a probe for an ultrasonic diagnostic apparatus is not limited to the sequence described above. The processes of the method may be performed in a different sequence or at the same time.

According to the embodiment, in manufacture of the probe 100 for an ultrasonic diagnostic apparatus, the piezoelectric member 130 is connected to the first connector 120 via the electrode layer 115 instead of using a complicated and laborious soldering operation, thereby enabling easy connection between the piezoelectric member 130 and the first connector 120 while preventing deterioration in performance caused by defective connection therebetween and in performance of the piezoelectric member 130 caused by heat during manufacture.

Further, according to the embodiment, the first connector 120 is bonded between the backing members 111, 112, instead of being disposed between a backing layer 110 and the piezoelectric member 130, to be electrically connected to the piezoelectric member 130 via the electrode layer 115, thereby preventing deterioration in performance caused by defective connection between the piezoelectric member 130 and the first connector 120 and preventing damage of the first connector 120 caused by bending.

Further, according to the embodiment, individual formation and maintenance of the backing layer 110 can be achieved by bonding the first connector 120 to the backing members 111, 112 and forming the electrode layer 115 thereon, so that the backing layer 110 can be prepared in desired shapes and dimensions so as to be easily assembled to other components, thereby enabling easy manufacture of the probe at lower cost while enhancing uniformity of final products.

Figure 7:
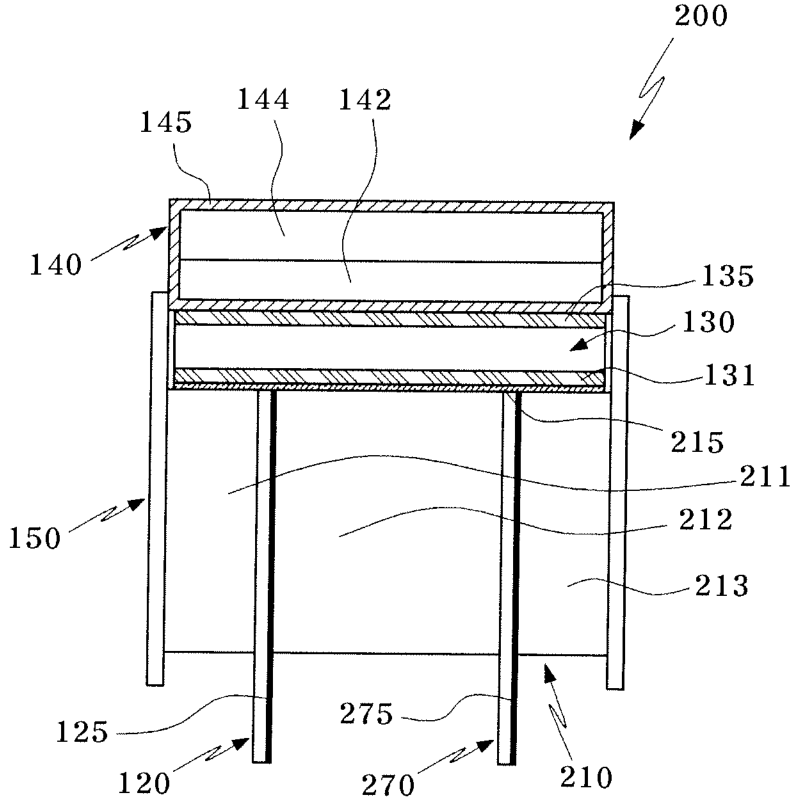
FIG. 7 is a schematic view of a probe for an ultrasonic diagnostic apparatus according to a second embodiment of the present invention.

FIG. 7 is a schematic view of a probe for an ultrasonic diagnostic apparatus according to a second embodiment of the invention.

For descriptive convenience, the same or similar components to those of the above embodiment will be denoted by the same reference numerals as those of the above embodiment, and a detailed description thereof will be omitted herein.

Referring to FIG. 7, a probe 200 for an ultrasonic diagnostic apparatus according to the second embodiment includes a backing layer 210, a first connector 120, a second connector 270, a piezoelectric member 130, a sound matching layer 140, and a ground connector 150.

The backing layer 210 is disposed behind the piezoelectric member 130. The backing layer 210 includes multiple backing members 211, 212, 213 and is formed by bonding the backing members 211, 212, 213 to each other. The backing layer 210 may be formed of a material containing a rubber to which epoxy, tungsten powder, and the like are added.

The first connector 120 is bonded between the backing members 211, 212. According to this embodiment, the first connector 120 is inserted and bonded between two backing members 211, 212 among the three backing members 211, 212, 213. The first connector 120 is disposed in the height direction of the backing members 211, 212, 213. The backing members 211, 212 are bonded to opposite sides of the first connector 120, respectively.

One end of the first connector 120 bonded between the backing members 211, 212 is exposed on a front side of the backing layer 210 adjacent to the piezoelectric member 130, and the other end thereof extends through a rear side of the backing layer 210. As such, since the one end of the first connector 120 is exposed on the front side of the backing layer 210, electrodes 125 of the first connector 120 are exposed on the front side of the backing layer 210.

The second connector 270 includes an insulation part (reference numeral omitted) and electrodes 275. The multiple electrodes 275 are disposed on the insulation part to be spaced from each other in the arrangement direction. According to this embodiment, the second connector 270 is inserted and bonded between the two backing members 212, 213. The second connector 270 is disposed in the height direction of the backing members 211, 212, 213. The backing members 212, 213 are bonded to opposite sides of the second connector 270, respectively.

One end of the second connector 270 bonded between the backing members 212, 213 is exposed on the front side of the backing layer 210 adjacent to the piezoelectric member 130, and the other end thereof extends through the rear side of the backing layer 210. As such, since the one end of the second connector 270 is exposed on a front side of the backing layer 210, the electrodes 275 of the second connector 270 are exposed from the backing layer 210.

As in the first electrode 120, the second connector 270 may include a flexible printed circuit board (FPCB), a printed circuit board or any configuration capable of supplying signals or electricity.

According to this embodiment, the first connector 120 is spaced from the second connector 270 by a width occupied by the backing member 212, and the electrodes 275 of the second connector 270 are disposed to alternate with the electrodes 125 of the first connector 120.

Each of the electrodes 125, 275 of the first and second connectors 120, 270 is a signal electrode that is electrically connected to a first electrode 131 of the piezoelectric member 130.

The backing layer 210 includes an electrode layer 215. The electrode layer 215 is formed on the backing layer 210 to be disposed between the backing layer 210 and the piezoelectric member 130. The electrode layer 215 is electrically connected to the electrodes 125, 275 of the first and second connectors 120, 270.

The piezoelectric member 130 may be composed of a plurality of piezoelectric members 130 arranged in an array to provide multiple channels. Accordingly, the electrode layer 215 may also be composed of a plurality of electrode layers 215 arranged side by side in an array so as to correspond to the piezoelectric members 130 arranged in an array. The piezoelectric members 130 and the electrode layers 215 are correspondingly connected to the electrodes 125, 275 spaced from each other in the arrangement direction.

The sound matching layer 140 is provided with an electrode part 145, which is electrically connected to the ground connector 150. In this embodiment, connection between the piezoelectric member 130 and the ground connector 150 is illustrated as being embodied by the electrode part 145 formed on the sound matching layer 140. However, the invention is not limited thereto and the connection between the piezoelectric member 130 and the ground connector 150 can be realized in various manners.

Figure 8:
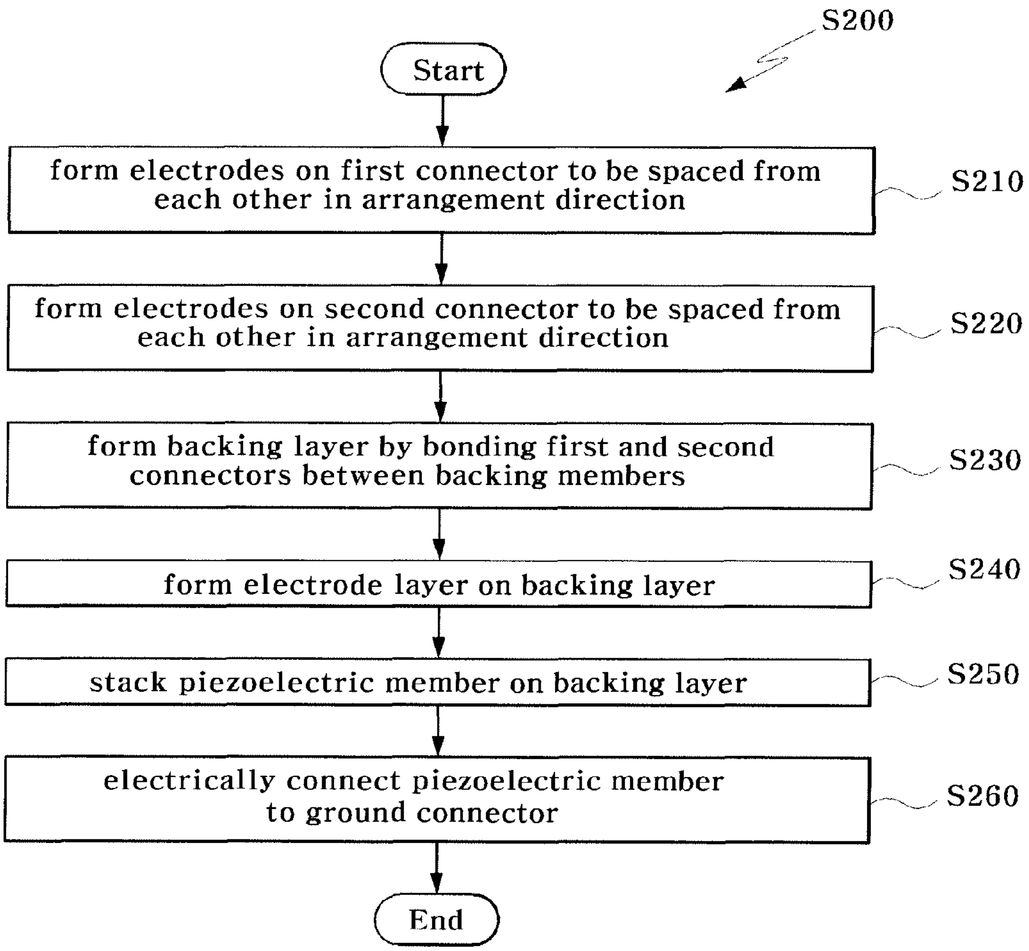
FIG. 8 is a flowchart of a method of manufacturing the probe for an ultrasonic diagnostic apparatus according to the second embodiment of the invention.
Figure 9:
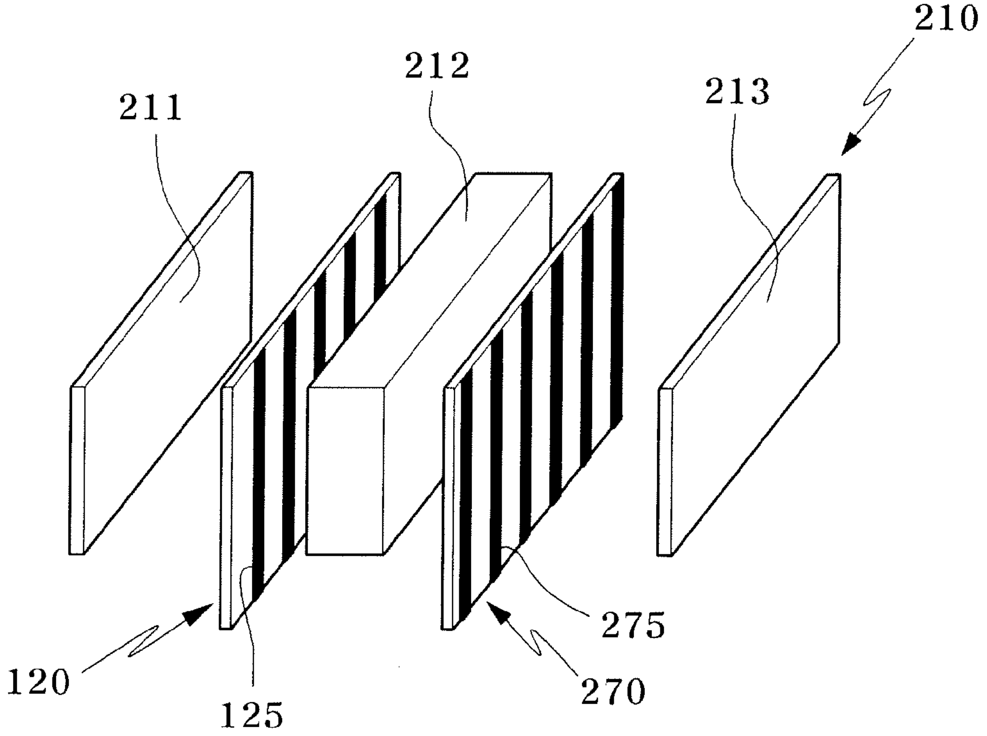
FIGS. 9 and 10 are views of a process of forming a backing layer of the probe according to the second embodiment of the invention.
Figure 10:
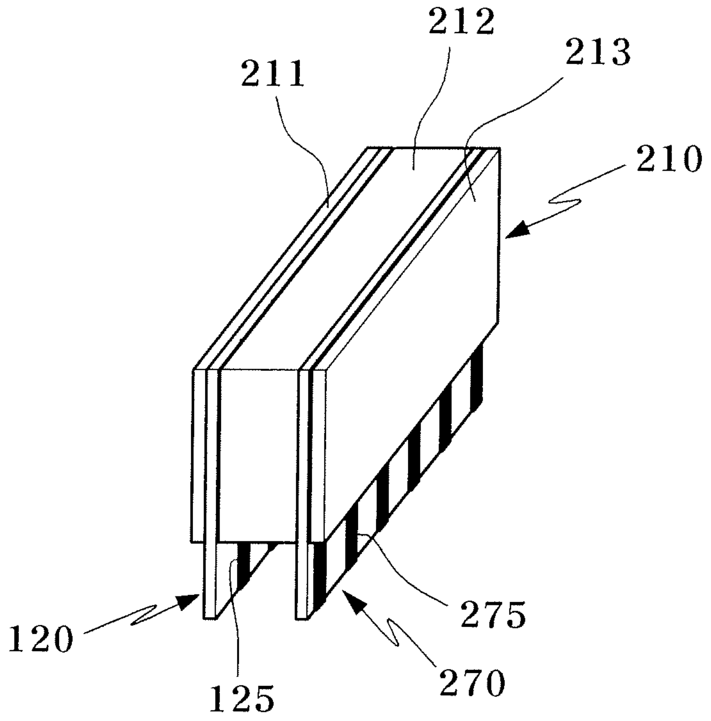
Figure 11:
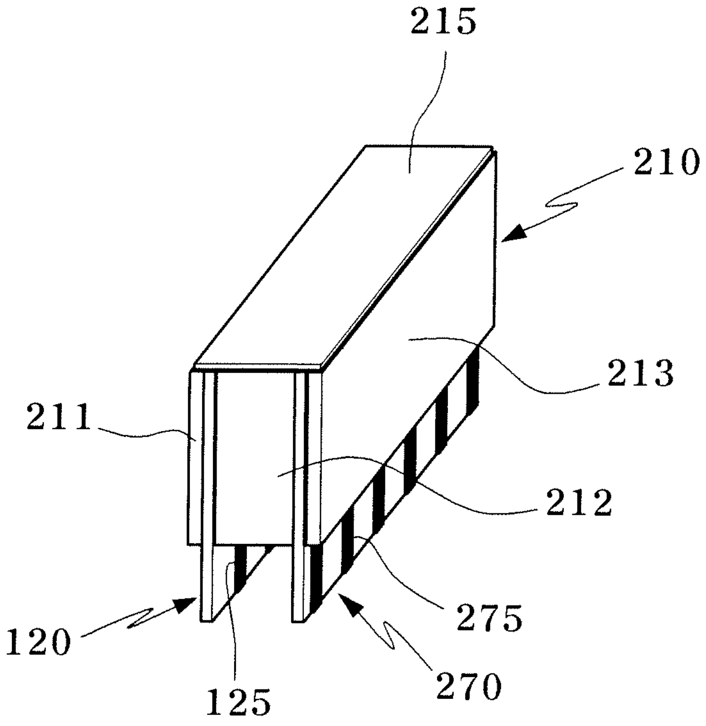
FIG. 11 is a view of a process of forming an electrode layer on the backing layer of the probe according to the second embodiment of the invention.

FIG. 8 is a flowchart of a method of manufacturing the probe for an ultrasonic diagnostic apparatus according to the second embodiment of the invention, FIGS. 9 and 10 are views of a process of forming the backing layer of the probe according to the second embodiment of the invention, and FIG. 11 is a view of a process of forming the electrode layer on the backing layer of the probe according to the second embodiment of the invention.

Referring to FIGS. 7 to 11, the method of manufacturing the probe for an ultrasonic diagnostic apparatus according to the second embodiment will now be described.

In the method S200 according to this embodiment, firstly, electrodes 125 are formed on a first connector 120 in S210, and electrodes 275 are formed on a second connector 270 in S220, as shown in FIG. 9.

Here, the respective electrodes 125, 275 of the first and second connectors 120, 270 are formed in the height direction of the backing members 211, 212, 213 and are spaced from each other in the arrangement direction of piezoelectric members 130 arranged in an array.

With the electrodes 125, 275 formed on the first and second connectors 120, 270, respectively, the first and second connectors 120, 270 are bonded between the backing members 211, 212, 213 to form a backing layer 210 in S230.

For this purpose, the backing members 211, 212, 213 are formed of a material including a rubber to which epoxy resin, tungsten powder, and the like are added. Then, with the first connector 120 disposed between the backing members 211, 212 in the height direction, the backing members 211, 212 are bonded to opposite sides of the first connector 120.

Further, with the second connector 270 disposed between the backing members 212, 213 in the height direction, the backing members 212, 213 are bonded to opposite sides of the second connector 270, thereby completing formation of the backing layer 210.

One end of each of the first and second connectors 120, 270 bonded between the backing members 211, 212, 213 is exposed on a front side of the backing layer 210 adjacent to the piezoelectric member 130, and the other end thereof extends through the rear side of the backing layer 210.

Since the one end of each of the first and second connectors 120, 270 is exposed on the front side of the backing layer 210, the electrodes 125, 275 of the first and second connectors 120, 270 are exposed on the front side of the backing layer 210.

According to this embodiment, when forming the backing layer 210, the first and second connectors 120, 270 may be disposed in the height direction of the backing members 211, 212, 213, such that the electrodes 275 of the second connector 270 alternate with the electrodes 125 of the first connector 120.

After the backing layer 210 is formed, an electrode layer 215 is formed on the backing layer 210 to be electrically connected to the piezoelectric member 130 and the electrodes 125, 275 of the first and second connectors 120, 270, as shown in FIG. 11, in S240.

With this configuration of the electrode layer 215, the rear side of the electrode layer 215 adjoining the surface of the backing layer 210 is electrically connected to the electrodes 125, 275 of the first and second connectors 120, 270.

After the electrode layer 215 is formed on the backing layer 210, the piezoelectric member 130 is stacked on the backing layer 210 to be electrically connected to the electrodes 125, 275 of the first and second connectors 120, 270 in S250.

By this process, a first electrode 131 of the piezoelectric member 130 is electrically connected to the electrode layer 215. As such, since the electrode layer 215 connected to the first electrode 131 is electrically connected to the electrodes 125, 275 of the first and second connectors 120, 270, the piezoelectric member 130 is electrically connected to the electrodes 125, 275 of the first and second connectors 120, 270 via the electrode layer 215 and the first electrode 131 which are electrically connected to each other.

As in the above embodiment, the piezoelectric member 130 of this embodiment may be divided into multiple piezoelectric members 130 spaced a predetermined distance from each other and arranged side by side in an array, so that the multiple piezoelectric members can be used as multiple channels corresponding to the multiple electrodes 125, 275 formed on the first and second connectors 120, 270.

The electrode layer 215 may also be divided into multiple electrode layers, which are arranged side by side in an array so as to correspond one-to-one to the first electrodes 131 formed on the multiple piezoelectric members 130.

According to this embodiment of the invention, stacks of the backing layer 210 and the piezoelectric member 130 are diced by a dicing machine (not shown). Dicing is performed to a depth such that the electrode layer 215 can be reliably divided into the multiple electrode layers.

By dicing, the piezoelectric member 130 is divided into the multiple piezoelectric members 130 spaced a predetermined distance from each other, such that first and second electrodes 131, 135 formed on each of the piezoelectric members 130 can be electrically completely separated from first and second electrodes 131, 135 formed on other piezoelectric members 130 adjacent thereto.

When the electrode layer 215 is divided into the multiple electrode layers 215 by dicing, each of the electrodes layers 215 is electrically completely separated from other electrode layers adjacent thereto such that one divided electrode layer 215 can be connected to a first electrode 131 formed on one piezoelectric member 130.

Figure 12:
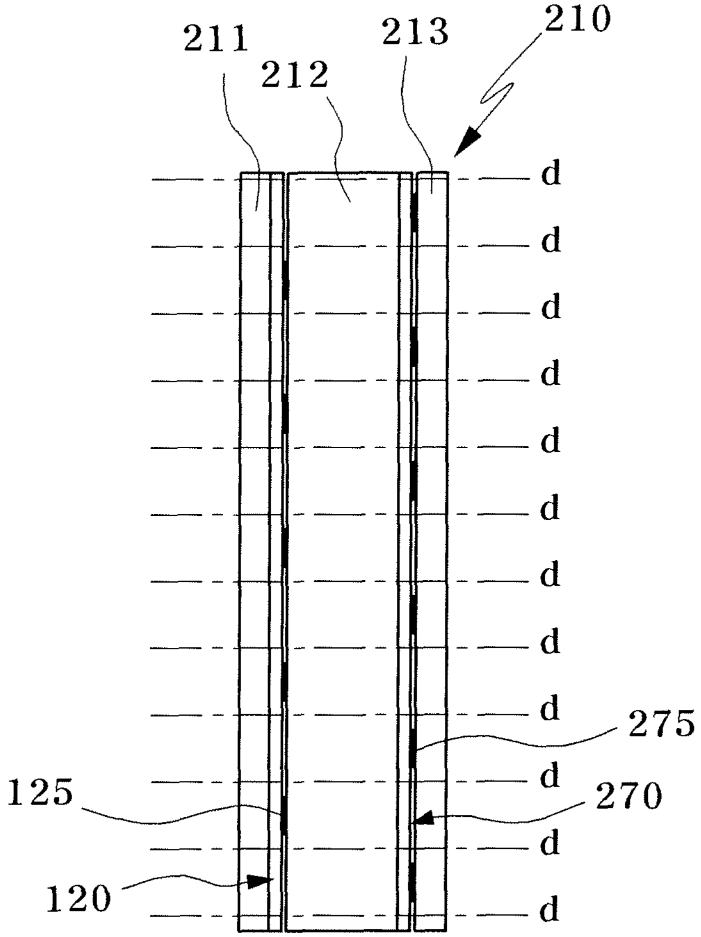
FIG. 12 is a view showing a separated state of the backing layer of the probe according to the second embodiment of the invention.

FIG. 12 is a view showing a separated state of the backing layer of the probe according to the second embodiment of the invention.

Referring to FIG. 12, separation between the backing layer and the first and second connectors by dicing will be described. In FIG. 12, the electrode layer is omitted.

In FIG. 12, by dicing the stacks of the backing layer 210 and the piezoelectric member 130 (see FIG. 7), the backing layer 210, the electrode layer 215 (see FIG. 7), and the first and second connectors 120, 270 electrically connected to the electrode layer 215 are divided as follows.

When the electrode layer 215 is divided into the multiple electrode layers 215 by dicing, each of the electrodes layers 215 is electrically completely separated from other electrode layers 215 adjacent thereto. Here, only one of the electrode 125 of the first connector 120 and the electrode 275 of the second connector 270 is connected to one electrode layer 115.

For this purpose, when the electrode layer 215 is divided by dicing, portions of the first connector 120 corresponding to center lines between the respective electrodes 125 of the first connector 120 disposed in the arrangement direction are divided and portions of the second connector 270 corresponding center lines between the respective electrodes 275 of the second connector 270 disposed in the arrangement direction are divided.

According to this embodiment, since the electrodes 125 of the first connector 120 are disposed to alternate with the electrodes 275 of the second connector 270, the respective dividing lines (d) formed on the electrode layer 215 to divide the electrode layer 215 by dicing are formed between the respective electrodes 125 of the first connector 120 and between the respective electrodes 275 of the second connector 270 disposed to alternate with the respective electrodes 125 of the first connector 120.

As a result, only one of the electrode 125 of the first connector 120 and the electrode 275 of the second connector 270 can be connected to one electrode layer 215.

After the piezoelectric member 130 is stacked on the backing layer 210, a sound matching layer 140 is stacked on the piezoelectric member 130 and the piezoelectric member 130 is electrically connected to a ground connector 150, as shown in FIG. 7, in S260. This operation is similar to that of the above embodiment, and a detailed description thereof will be omitted herein.

The method S200 of manufacturing a probe for an ultrasonic diagnostic apparatus is not limited to the sequence described above. The processes of the method may be performed in a different sequence or at the same time.

According to the embodiment, in manufacture of the probe 200 for an ultrasonic diagnostic apparatus, the piezoelectric member 130 is electrically connected to the first and second connectors 120, 270, that is, multiple connectors 120, 270, so that a distance between the first and second connectors 120, 270 and the ground connector 150 can be decreased.

As a result, the probe 200 according to this embodiment has a narrow space between the electrodes 125, 275 of the first and second connectors 120, 270, that is, signal electrodes, and the electrode of the ground connector 150, that is, a ground electrode, thereby reducing noise.

Further, according to the embodiment, the multiple connectors 120, 270 are bonded in the backing layer 210 and the electrodes 125 of the first connector 120 are disposed to alternate with the electrodes 275 of the second connector 270, so that the respective components of the probe 200 divided by dicing may have sufficient strength and be arranged at a narrower pitch to have a high density and a small size.

Figure 13:
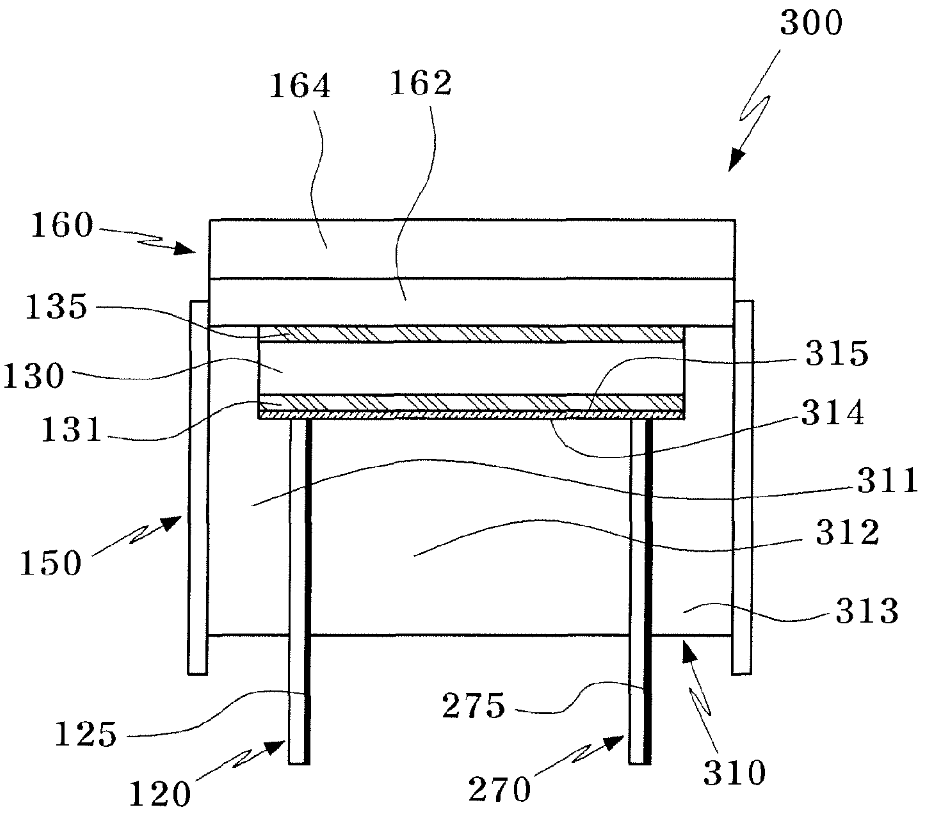
FIG. 13 is a schematic view of a probe for an ultrasonic diagnostic apparatus according to a third embodiment of the present invention.

FIG. 13 is a schematic view of a probe for an ultrasonic diagnostic apparatus according to a third embodiment of the present invention.

For descriptive convenience, the same or similar components to those of the above embodiment will be denoted by the same reference numerals as those of the above embodiment, and a detailed description thereof will be omitted herein.

Referring to FIG. 13, a probe 300 for an ultrasonic diagnostic apparatus according to the third embodiment includes a backing layer 310, a first connector 120, a second connector 270, a piezoelectric member 130, a sound matching layer 160, and a ground connector 150.

The backing layer 310 is disposed behind the piezoelectric member 130. The backing layer 310 includes multiple backing members 311, 312, 313 and is formed by bonding the backing members 311, 312, 313, the first connector 120 and the second connector 270 to each other.

According to this embodiment, a mounting groove 314 is formed on the backing layer 310. The mounting groove 314 is formed on the front side of the backing layer 310 adjacent to the piezoelectric member 130. The piezoelectric member 130 is inserted into the mounting groove 314. The mounting groove 314 is depressed into the backing layer 310 in a shape corresponding to the piezoelectric member 130 to allow the piezoelectric member 130 to be inserted into the backing layer 310.

The backing layer 310 includes an electrode layer 315. The electrode layer 315 is formed on the backing layer 310 and is disposed between the backing layer 310 and the piezoelectric member 130. Specifically, the electrode layer 315 may be formed on the mounting groove 314 and disposed to be electrically connected to electrodes 125, 275 of the first and second connectors 120, 270.

The sound matching layer 160 is disposed in front of the piezoelectric member 130. The sound matching layer 160 is stacked on a plane constituted by the backing layer 310 and the piezoelectric member 130 inserted into the mounting groove 314 of the backing layer 310.

The sound matching layer 160 includes first and second sound matching layers 162, 164 and is directly connected to the piezoelectric member 130. The sound matching layer 160 is formed of an electrically conductive material, such as graphite, gold, silver or copper, and is electrically connected to the second electrode 135 of the piezoelectric member 130.

The sound matching layer 160 may be entirely or partially formed of the electrically conductive material. When the sound matching layer 160 is partially formed of the electrically conductive material, the first sound matching layer 162 adjacent to the piezoelectric member 130 may be formed of the electrically conductive material.

In this embodiment, connection between the piezoelectric member 130 and the ground connector 150 is illustrated as being obtained by the first sound matching layer 162 of the sound matching layer 160. However, the invention is not limited thereto and the connection therebetween can be realized in various manners.

Figure 14:
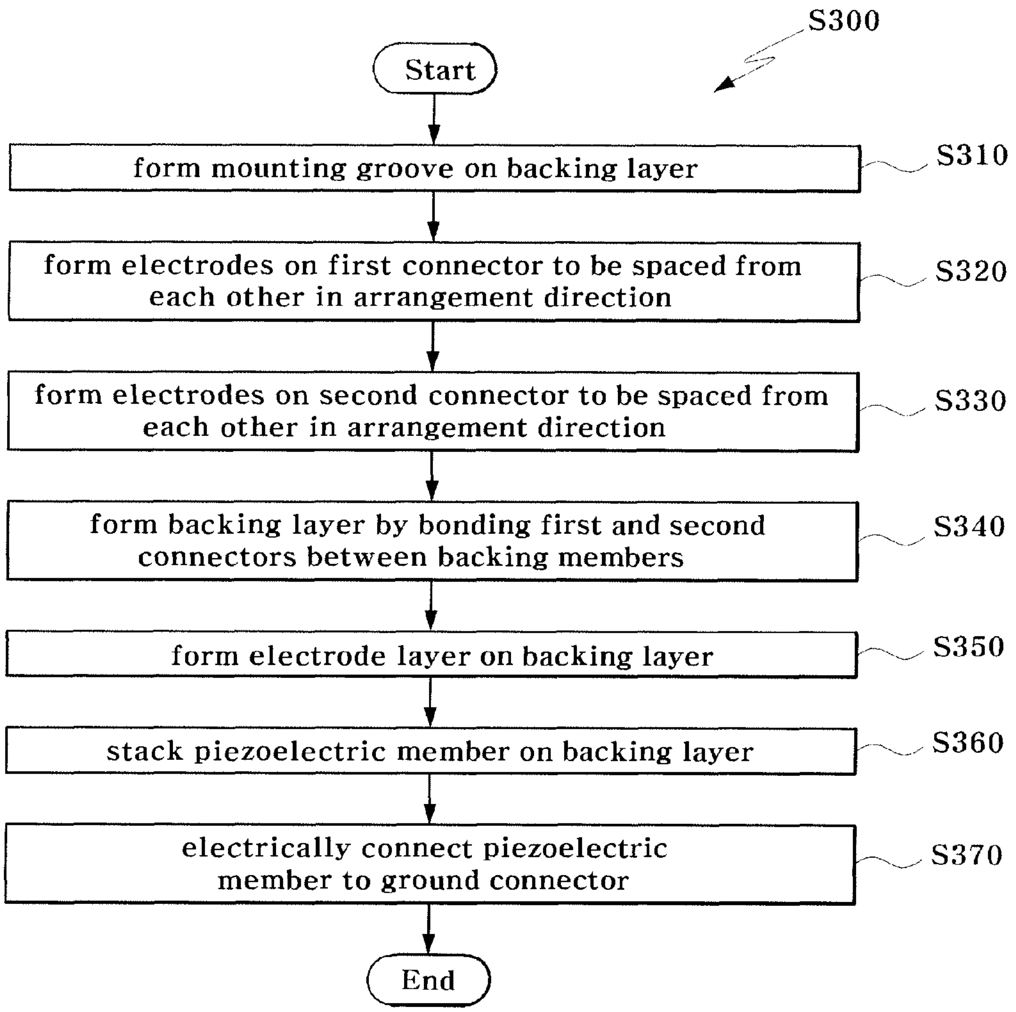
FIG. 14 is a flowchart of a method of manufacturing the probe for an ultrasonic diagnostic apparatus according to the third embodiment of the present invention.

FIG. 14 is a flowchart of a method of manufacturing the probe for an ultrasonic diagnostic apparatus according to the third embodiment of the present invention.

Referring to FIGS. 13 to 14, the method of manufacturing the probe for an ultrasonic diagnostic apparatus according to the third embodiment will now be described.

In the method S300 according to this embodiment, firstly, a mounting groove 314 is formed on a backing layer 310 in S310.

For example, in order to form the mounting groove 314 on backing members 311, 312, 313 formed of a material including a rubber to which epoxy resin, tungsten powder, and the like are added, the backing members 311, 313 are formed to have steps at both sides of the backing member 312 interposed between the backing members 311, 313. The backing members 311, 313 are disposed adjacent to the backing layer 312 by forming lower step sections to be coplanar with the backing layer 312 interposed between the backing members 311, 313.

Then, electrodes 125 are formed on a first connector 120 in S320, and electrodes 275 are formed on a second connector 270 in S330.

Here, the respective electrodes 125, 275 of the first and second connectors 120, 270 are formed in the height direction of the backing members 311, 312, 313 and are spaced from each other in the arrangement direction of piezoelectric members 130 arranged in an array.

With the electrodes 125, 275 formed on the first and second connectors 120, 270, respectively, the first and second connectors 120, 270 are bonded between backing members 311, 312, 313 to form a backing layer 310 in S340.

For this purpose, with the first connector 120 disposed between the backing members 311, 312 in the height direction, the backing members 311, 312 are bonded to opposite sides of the first connector 120. Further, with the second connector 270 disposed between the backing members 312, 313 in the height direction, the backing members 312, 313 are bonded to opposite sides of the second connector 270, thereby completing formation of the backing layer 310.

One end of each of the first and second connectors 120, 270 bonded between the backing members 311, 312, 313 is exposed on the front side of the backing layer 310 adjacent to the piezoelectric member 130, and the other end thereof extends through the rear side of the backing layer 310.

Since the one end of each of the first and second connectors 120, 270 is exposed on the front side of the backing layer 310, the electrodes 125, 275 of the first and second connectors 120, 270 are exposed on the front side of the backing layer 310 through the mounting groove 314.

After the backing layer 310 is formed, an electrode layer 315 is formed on the backing layer 310 to be electrically connected to the piezoelectric member 130 and the electrodes 125, 275 of the first and second connectors 120, 270 in S350. The electrode layer 315 may be formed on the mounting groove 314.

With this configuration of the electrode layer 315, the rear side of the electrode layer 315 adjoining the surface of the mounting groove 314 is electrically connected to the electrodes 125, 275 of the first and second connectors 120, 270.

After the electrode layer 315 is formed on the backing layer 310, the piezoelectric member 130 is stacked on the backing layer 310 by inserting the piezoelectric member 130 into the mounting groove 314 to be electrically connected to the electrodes 125, 275 of the first and second connectors 120, 270 in S360.

By this process, a first electrode 131 of the piezoelectric member 130 is electrically connected to the front side of the electrode layer 315. As such, since the electrode layer 315 connected to the first electrode 131 is electrically connected at the rear side thereof to the electrodes 125, 275 of the first and second connectors 120, 270, the piezoelectric member 130 is electrically connected to the electrodes 125, 275 of the first and second connectors 120, 270 via the electrode layer 315 and the first electrode 131 which are electrically connected to each other.

As in the above embodiment, after the piezoelectric member 130 is stacked on the backing layer 310, a sound matching layer 160 is stacked on the piezoelectric member 130 and the piezoelectric member 130 is electrically connected to a ground connector 150 in S370. This operation is similar to that of the above embodiment, and a detailed description thereof will be omitted herein.

The method S300 of manufacturing a probe for an ultrasonic diagnostic apparatus is not limited to the sequence described above. The processes of the method may be performed in a different sequence or at the same time.

According to this embodiment of the invention, in the probe 300 for an ultrasonic diagnostic apparatus, the mounting groove 314 is formed on the backing members 311, 312, 313 such that the piezoelectric member 130 can be inserted into the mounting groove to reduce the size of the probe and allow easy connection between the piezoelectric member 130 and the first and second connectors 120, 270 while ensuring an enhanced support structure of the piezoelectric member 130, thereby preventing defective connection and deterioration in performance of the probe caused thereby.

As apparent from the description, according to one embodiment of the invention, a piezoelectric member is joined to a first connector or to first and second connectors via an electrode layer instead of using a complicated and laborious soldering operation in manufacture of the probe, thereby enabling easy connection between the piezoelectric member and the connector while preventing deterioration in performance caused by defective connection therebetween and deterioration in performance of the piezoelectric member caused by heat during manufacture.

Further, according to one embodiment of the invention, the first connector or the first and second connectors are bonded between backing members, instead of being disposed between a backing layer and the piezoelectric member, to be electrically connected to the piezoelectric member via the electrode layer, thereby preventing deterioration in performance caused by defective connection between the piezoelectric member and the first or second connector and preventing damage of the first and second connectors caused by bending.

Further, according to one embodiment of the invention, individual formation and maintenance of the backing layer can be achieved by bonding the first and second connectors to the backing members and forming the electrode layer thereon, so that the backing layer can be prepared in desired shapes and dimensions so as to be easily assembled to other components, thereby enabling easy manufacture of the probe at lower cost while enhancing uniformity of final products.

Further, according to one embodiment of the invention, the probe has a narrow space between signal electrodes and ground electrodes, thereby reducing noise.

Further, according to one embodiment of the invention, electrodes of the first connector alternate with those of the second connector, so that respective components divided by dicing have sufficient strength at a narrower pitch to have a high density and a small size.

Further, according to one embodiment of the invention, the piezoelectric member is inserted into a mounting groove formed on the backing layer, thereby enabling size reduction and easy connection between the piezoelectric member and the first and second connectors while providing a more rigid support structure to the piezoelectric member to prevent deterioration in performance caused by defective connection therebetween.

In understanding the scope of the invention, the terms "part" or "member" when used in the singular can have the dual meaning of a singular part or a plurality of parts unless otherwise stated. Further, the use of articles "a," "an" and "the" in the context of describing the invention, especially in the context of the embodiments, are to be construed to cover both the singular and the plural unless otherwise indicated herein or clearly contradicted by context.

Although some embodiments have been provided to illustrate the invention in conjunction with the drawings, it will be apparent to those skilled in the art that the embodiments are given by way of illustration only, and that various modifications and equivalent embodiments can be made without departing from the spirit and scope of the invention. Accordingly, the scope of the invention should be limited only by the accompanying claims.

What is claimed is:

1. A probe for an ultrasonic diagnostic apparatus, comprising:

a backing layer including backing members;

a first connector bonded between the backing members in a height direction, and including first connector electrodes spaced from each other in an arrangement direction;

a second connector bonded between the backing members in the height direction, and including second connector electrodes spaced from each other in the arrangement direction; and a piezoelectric member electrically connected to the first connector electrodes and the second connector electrodes, wherein:

the second connector is disposed such that the first connector electrodes alternate with the second connector electrodes in the arrangement direction, whereby the first connector electrodes do not overlap the second connector electrodes in the height direction, and the first connector and the second connector are separated from each other.

2. The probe according to claim 1, wherein the first connector comprises a flexible printed circuit board (FPCB).

3. The probe according to claim 1, wherein the backing layer comprises an electrode layer electrically connected to the first connector electrodes and the second connector electrodes.

4. The probe according to claim 3, wherein the electrode layer is disposed on a surface of the backing layer.

5. The probe according to claim 1, wherein the backing layer has a mounting groove and the piezoelectric member is disposed in the mounting groove.

6. The probe according to claim 1, wherein the first connector electrodes and the second connector electrodes are signal electrodes.

7. A method of manufacturing a probe for an ultrasonic diagnostic apparatus, comprising:

forming first connector electrodes spaced from each other in an arrangement direction on a first connector;

forming second connector electrodes spaced from each other in the arrangement direction on a second connector;

forming a backing layer by bonding the first and second connectors between backing members in a height direction; and stacking a piezoelectric member on the backing layer such that the piezoelectric member is electrically connected to the first connector electrodes and the second connector electrodes, wherein the forming a backing layer comprises disposing the second connector such that the first connector electrodes alternate with the second connector electrodes in the arrangement direction, whereby the first connector electrodes do not overlap the second connector electrodes in the height direction, and the first connector and the second connector are separated from each other.

8. The method according to claim 7, further comprising:

after forming the backing layer, forming an electrode layer on the backing layer such that the electrode layer is electrically connected to the piezoelectric member, the first connector electrodes and the second connector electrodes.

9. The method according to claim 7, further comprising:

forming a mounting groove on the backing layer, wherein the stacking a piezoelectric member on the backing layer comprises inserting the piezoelectric member into the mounting groove.

* * * * *